(12) United States Patent
Hsu et al.

(10) Patent No.: US 11,954,854 B2
(45) Date of Patent: Apr. 9, 2024

(54) RETINA VESSEL MEASUREMENT

(71) Applicants: National University of Singapore, Singapore (SG); Singapore Health Services Pte Ltd, Singapore (SG)

(72) Inventors: Wynne Hsu, Singapore (SG); Mong Li Lee, Singapore (SG); Dejiang Xu, Singapore (SG); Tien Yin Wong, Singapore (SG); Yim Lui Cheung, Hong Kong (CN)

(73) Assignees: National University of Singapore, Singapore (SG); Singapore Health Services Pte Ltd, Singapore (SG)

( * ) Notice: Subject to any disclaimer, the term of this patent is extended or adjusted under 35 U.S.C. 154(b) by 435 days.

(21) Appl. No.: 17/429,109

(22) PCT Filed: Feb. 11, 2020

(86) PCT No.: PCT/SG2020/050067
§ 371 (c)(1),
(2) Date: Aug. 6, 2021

(87) PCT Pub. No.: WO2020/167251
PCT Pub. Date: Aug. 20, 2020

(65) Prior Publication Data
US 2022/0130037 A1    Apr. 28, 2022

(30) Foreign Application Priority Data

Feb. 12, 2019  (SG) ............................. 10201901218S

(51) Int. Cl.
*G06T 7/12* (2017.01)
*G06T 7/00* (2017.01)
(Continued)

(52) U.S. Cl.
CPC .......... *G06T 7/0012* (2013.01); *G06V 10/454* (2022.01); *G06V 10/764* (2022.01);
(Continued)

(58) Field of Classification Search
CPC ......... G06T 7/0012; G06T 2207/20081; G06T 2207/20084; G06T 2207/30041;
(Continued)

(56) References Cited

U.S. PATENT DOCUMENTS 9,468,377 B2 * 10/2016 Stamile .................. G06T 7/194
2019/0180441 A1   6/2019 Peng et al.

FOREIGN PATENT DOCUMENTS

CN      108520522 A    9/2018
WO      2019022663 A1  1/2019

OTHER PUBLICATIONS

The International Search Report and The Written Opinion of the International Searching Authority for PCT/SG2020/050067, dated Jun. 16, 2020.
(Continued)

*Primary Examiner* — Charlotte M Baker
(74) *Attorney, Agent, or Firm* — Botos Churchill IP Law LLP

(57) ABSTRACT

Disclosed is a method for training a neural network to quantify the vessel calibre of retina fundus images. The method involves receiving a plurality of fundus images; pre-processing the fundus images to normalise images features of the fundus images; and training a multi-layer neural network, the neural network comprising of a convolutional unit, multiple dense blocks alternating with transition units for down-sampling image features determined by the neural network, and a fully-connected unit, wherein each dense
(Continued)

block comprises a series of cAdd units packed with multiple convolutions, and each transition layer comprises a convolution with pooling.

19 Claims, 10 Drawing Sheets

(51) Int. Cl.
    *G06V 10/44*     (2022.01)
    *G06V 10/764*     (2022.01)
    *G06V 10/82*     (2022.01)
    *G06V 40/18*     (2022.01)

(52) U.S. Cl.
    CPC ............ *G06V 10/82* (2022.01); *G06V 40/193* (2022.01); *G06V 40/197* (2022.01); *G06T 2207/20081* (2013.01); *G06T 2207/20084* (2013.01); *G06T 2207/30041* (2013.01); *G06V 2201/03* (2022.01)

(58) Field of Classification Search
    CPC .... G06V 10/454; G06V 10/764; G06V 10/82; G06V 40/193; G06V 40/197; G06V 2201/03; G06F 18/24317; G06N 3/045; G06N 3/048; G06N 3/082; G16H 30/40; G16H 50/20

USPC ........................................................ 382/128
See application file for complete search history.

(56) References Cited

OTHER PUBLICATIONS

Grassman, et al., "A Deep Learning Algorithm for Prediction of Age-Related Eye Disease Study Severity Scale for Age-Related Macular Degeneration from Color Fundus Photography", Ophthalmology, 2018, vol. 125, No. 9, pp. 1410-1420.

Huang, et al., "Densely Connected Convolutional Networks", 2017 IEEE Conference on Computer Vision and Pattern Recognition, 2017, pp. 1-9.

Gulshan, et al., "Development and Validation of a Deep Learning Algorithm for Detection of Diabetic Retinopathy in Retinal Fundus Photographs", JAMA, Original Investigation, Innovations in Health Care Delivery, Nov. 29, 2016, pp. E1-E9.

Poplin, et al., "Predicting Cardiovascular Risk Factors from Retinal Fundus Photographs using Deep Learning", 2018.

Varadarajan, et al., "Predicting Optical Coherence Tomography-derived Diabetic Macular Edema Grades From Fundus Photographs Using Deep Learning", Nature Communications, 2020, pp. 1-8.

* cited by examiner

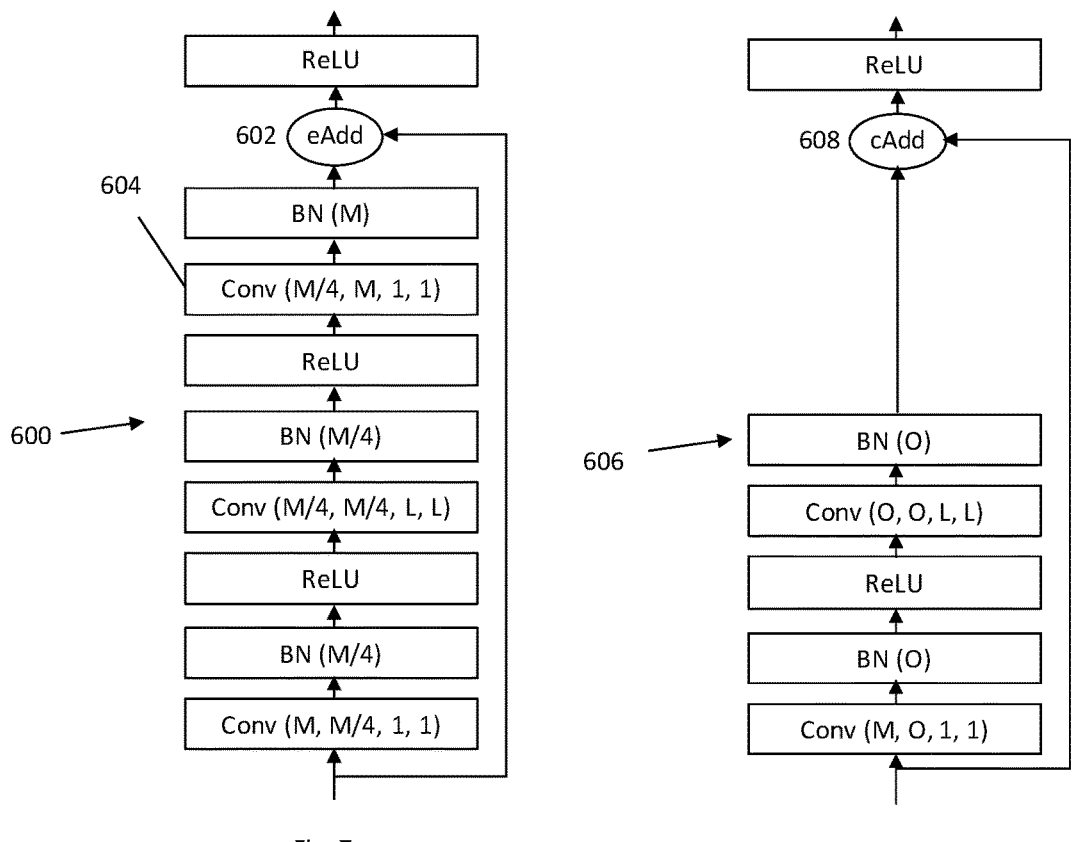
Fig. 7a
eAdd
Fig. 7b
cAdd
Fig. 7
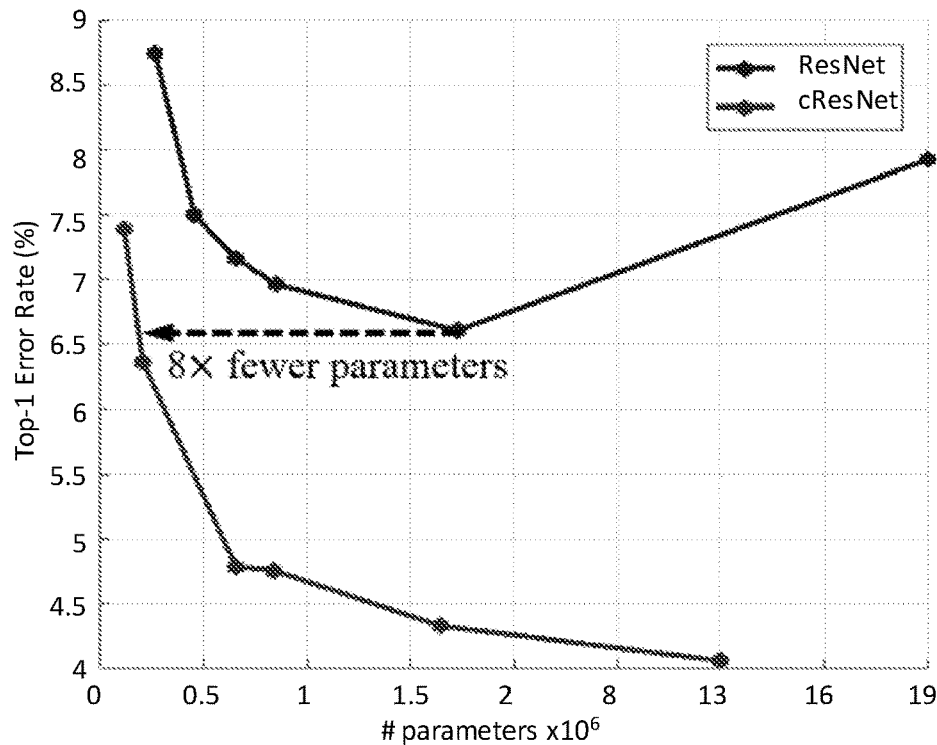
Fig. 8

US 11,954,854 B2

RETINA VESSEL MEASUREMENT

CROSS-REFERENCE TO RELATED APPLICATIONS

The present application is a national phase entry under 35 U.S.C. § 371 of International Application No. PCT/SG2020/050067, Feb. 11, 2020, published as International Publication No. WO 2020/167251 A1, which claims the benefit of the filing date of Singapore Patent Application No. 10201901218S filed Feb. 12, 2019, the disclosures of which are hereby incorporated by reference.

TECHNICAL FIELD

The present invention relates to deep learning systems for automated retina vessel measurement from fundus photographs.

BACKGROUND

Clinical studies have provided indications that changes in the retinal vascular structure are early warnings of potential cardiovascular disease (CVD) and other conditions such as dementia and diabetes. This is because the conditions of retinal arterioles and venules reflect the conditions of the blood vessels in the rest of the body.

Currently, grading of retinal photographs by human assessors are challenged by implementation issues, availability and training of assessors and long-term financial sustainability. Deep learning systems (DLS) have been proposed as an option for large-scale analysis of retinal images. DLS utilize artificial intelligence and representation-learning methods to process natural raw data, recognizing intricate structures in high-dimensional information. In contrast to traditional pattern recognition type software to detect specific images, patterns and lesions, DLS uses large datasets to enable mining, extraction and machine learning of meaningful patterns or features.

The performance of DLS partly depends on the connectedness of layers of the neural networks that extract features from the images. The greater the number of available features, the higher the confidence in the assessment. However, this comes at a cost of memory and other computer resources. There are also problems arising when seeking to train the neural network, in ensuring error is back propagated through the neural network—e.g. the vanishing gradient problem.

Therefore, it is desirable to provide a way for DLS to be trained by a wide variety of retinal images in order to address the problems mentioned in existing prior art and/or to provide the public with a useful choice.

SUMMARY OF THE INVENTION

This invention relates to a novel deep learning system for automated retina vessel measurement for the non-invasive observation of cardiovascular disorders. In particular, embodiments of the present invention relate to methods for obtaining retina image characteristics as well as automatic computation of measures that are correlated with medical conditions on the basis of retinal blood vessel characteristics.

Disclosed herein is a method for training a neural network for automated retina vessel measurement, comprising:
receiving a plurality of fundus images;
pre-processing the fundus images to normalise images features of the fundus images; and
training a multi-layer neural network, the neural network comprising of a convolutional unit, multiple dense blocks alternating with transition units for down-sampling image features determined by the neural network, and a fully-connected unit, wherein each dense block comprises a series of cAdd units packed with multiple convolutions, and each transition layer comprises a convolution with pooling.

The method may further comprise grouping the input channels of each cAdd unit into non-overlapping groups and adding the outputs of the cAdd unit to one of the non-overlapping groups thus forming the inputs to a next cAdd unit in the series, and for successive ones of said cAdd units, the output of a previous cAdd unit in the series is added to a different one of said non-overlapping groups. In the present context, the cAdd units form a series. During processing, the input is given to the first cAdd unit in the series and that unit processes the input and passes it to the next cAdd unit in the series, and so on until the last cAdd unit. As a consequence, it will be understood that each cAdd unit in a given series (with the exception of the first cAdd unit) will have a "previous" cAdd unit, being the unit from which it receives the output. It will similarly be understood that each cAdd unit in a given series (with the exception of the last cAdd unit) will have a "next" cAdd unit to which it passes its output.

The method may comprise automatically detecting a centre of an optic disc in each fundus image, and cropping the respective image to a region of predetermined dimensions centred on the optic disc centre.

Pre-processing the fundus images may comprise applying global contrast normalisation to each fundus image. Pre-processing the fundus images may further comprise median filtering using a kernel of predetermined size.

There are preferably five dense blocks in the multiple dense blocks. Each dense block may comprise a series of cAdd units packed with two types of convolutions. The two types of convolutions may comprise a 1×1 convolution and a 3×3 convolution.

The convolution of each transition layer may be a 1×1 convolution

Also disclosed herein is a method of quantifying the vessel calibre of a retina fundus image, comprising:
receiving a retina fundus image; and
applying a neural network trained according to the method described above, to the retina fundus image.

Also disclosed herein is a computer system for training a neural network to generate retina vessel measurements, comprising:
memory; and
at least one processor, the memory storing a multi-layer neural network and instructions that, when executed by the at least one processor cause the at least one processor to:
receive a plurality of fundus images;
pre-process the fundus images to normalise images features of the fundus images; and
train the neural network on the pre-processed fundus images, the neural network comprising a convolutional unit, multiple dense blocks alternating with transition units for down-sampling image features determined by the neural network, and a fully-connected unit, wherein each dense block comprises a series of cAdd units packed with multiple convolutions, and each transition layer comprises a convolution with pooling.

The instructions may further cause the processor to group the input channels of each cAdd unit into non-overlapping groups and adding the outputs of the cAdd unit to one of the non-overlapping groups thus forming the inputs to a next cAdd unit in the series, and for successive ones of said cAdd units, the output of a previous cAdd unit in the series is added to a different one of said non-overlapping groups.

The instructions may further cause the processor to:
automatically detect a centre of an optic disc in each fundus image; and
crop the respective image to a region of predetermined dimensions centred on the optic disc centre.

The instructions may cause the processor to pre-process the fundus images by applying global contrast normalisation to each fundus image.

There may be five dense blocks in the multiple dense blocks. Each dense block may comprise a series of cAdd units packed with two types of convolutions. Two types of convolutions may comprise a 1×1 convolution and a 3×3 convolution.

The convolution of each transition layer may be a 1×1 convolution.

The neural network may be trained on the pre-processed fundus images to quantify the vessel calibre of a retina fundus image.

BRIEF DESCRIPTION OF THE DRAWINGS

Some embodiments will now be described by way of non-limiting example only, with reference to the accompanying drawings in which:

FIG. 7 illustrates a bottleneck unit using different propagation mechanisms;

FIG. 8 shows the performance of ResNet vs. cResNet on CIFAR-10;

DETAILED DESCRIPTION

Described herein is a system that utilizes deep learning to estimate the retinal vascular parameters—e.g. vessel caliber and other measurements such as, for example, vessel density. This method has been developed and tested with ~10,000 retinal images from various population-based studies. It can be effectively utilized for the large-scale grading of population-based studies. This represents broad time and cost-savings for clinician researchers. In addition, the system is not constrained to a certain population/ethnicity, due to the breadth of training data used. It can be utilized as-is on general populations. This removes geographical limitations on clinician researchers, and thereby makes the system able to be usefully applied in a cloud-based platform accessible from anywhere.

Embodiments of the method, and system executing that method, employ pre-processing to normalise image factors. The method is thereby not constrained to a certain model/type of retinal fundus camera. The method can be utilized as-is on any optic-disc centered retinal image with sufficient field-of-view.

Previous systems, such as that described in WO 2019/022663, the entire contents of which is incorporated herein by reference, provide a semi-automated platform for large-scale grading of retina images. However, manual inputs are often needed to localize the optic disc, correct vessel type and edit the traced vessel and segment widths. Embodiments disclosed herein eliminate such manual inputs, thus allowing retina images to be graded more easily and quickly and leading to significant time savings for population-based studies. This automated grading system has the advantages of being available on-demand, and guaranteeing perfectly replicable results.

Figure 13:
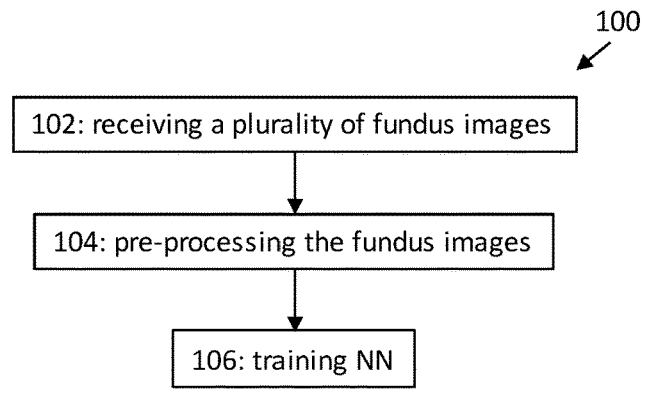
FIG. 13 illustrates a method for training a neural network to classify fundus images, and for subsequently classifying fundus images.

A method 100 to achieve this is set out in FIG. 13. The method 100 is used for training a neural network for automated retina vessel measurement and broadly comprises:
Step 102: receiving a plurality of fundus images;
Step 104: pre-processing the fundus images to normalise images features of the fundus images; and
Step 106: training a multi-layer neural network on the pre-processed fundus images, the neural network comprising of a convolutional unit, multiple dense blocks alternating with transition units for down-sampling image features determined by the neural network, and a fully-connected unit, wherein each dense block comprises a series of cAdd units packed with multiple convolutions, and each transition layer comprises a convolution with pooling.

The method 100 and system implementing it enable computation of quantifiable measures in a retina image for large-scale grading of retinal fundus images. As a result:
a) The steps achieving pre-processing of input retinal images minimises deleterious aspects of the retinal images and standardize retinal image grading;
b) The multi-layer neural network forms a deep learning architecture for the quantification of retinal vessel parameters; and
c) The method can be implemented on a cloud-based platform to facilitate large-scale population studies over time.

The pre-processing step 104 is intended to remove variance caused by changes in lighting, camera, angle and other factors in the fundus images. In other words, the pre-processing step 102 is intended to remove confounding effects of noise features in the fundus images.

The vessel width in the retina image is measured based on the number of pixels. However, the units for the vessel parameters such as CRAE and CRVE are in terms of microns. Each image has an Image Conversion Factor (ICE) that gives the mapping from the number of pixels to microns. Images from different fundus cameras may have different ICF due to magnification effects, image resolution and other reasons.

The present method standardizes each image by resizing it. In one embodiment, resizing occurs using the ratio cf/16.38 where cf is the ICF of the image and 16.38 is ICF of a standardized image. The images are thereby all brought to the same dimensions and pixel to micron mapping.

The present pre-processing step 104 further involves automatically detecting a centre of an optic disc in each fundus image, and cropping the respective image to a region of predetermined dimensions centred on the optic disc centre. In particular, step 104 involves region cropping to focus the neural network training, and any subsequent assessment of retina fundus, on features of the optic disc. The optic disc detection algorithm is described in WO 2019/022663 and is incorporated herein by reference. That optic disc detection algorithm is applied to the ICF standardized image to locate the optic disc centre. The image is then cropped to a region of predetermined dimensions—e.g. a 512*512 region—centred at the optic disc.

Once the optic disc has been identified and the image cropped to a standard region size, the images are normalised to remove noise resulting from, for example, variations in camera calibration and camera type. To achieve this, a global contrast normalization is applied on the cropped image to decrease the colour variation among the retina images from different races.

The total range of contrast across the image is scaled to a scaling factor, to normalise contrast variation, and each pixel contrast is then scaled using the same scaling factor.

After contrast normalisation, the images are filtered to remove noise. Presently, a median filtering is used with kernel of predetermined size—e.g. 5 pixels.

After the images are pre-processed according to step 104, they are used in training to quantify retinal vessel parameters. A deep learning architecture is used for that quantification. Notably, step 106 involves a propagation mechanism called channel-wise addition. As mentioned above, the input is the pre-processed to produce 512*512 cropped images. The pre-processed images are then passed to a neural network to train the neural network—step 106. The output of the neural network is a fully connected layer with the predicted caliber (craeB, craeC, crveB, crveC) or other measurement(s) of the input image. The neural network can have various compositions but comprises at least a convolutional unit followed by multiple dense blocks (presently there are five) that alternate with transition units to down-samples the features, and a fully-connected unit. Each dense block comprises or is a series of channel-wise addition (cAdd) packed with multiple convolutions (presently two types of convoluations—in the example shown these are 1×1 and 3×3). Each transition unit presently comprises a convolution (in the embodiment shown, it is 1×1) with pooling.

In the neural network, channel-wise addition (cAdd) is applied to each image before passing it through a convolution layer and max pooling—presently, the convolution layer uses a 7×7 window and stride length of 2, and the max pooling layer uses a 3×3 window with stride length of 2.

The convolution layer in the present embodiment is followed by a series of five dense blocks that alternate with transition layers/units. The transition units down-sample the features—i.e. the features detected by previous layers/units in the neural network. Each dense block comprises a series of units. Each transition layer comprises a convolution followed by average pooling—presently the convolution is a 1×1 convolution followed by a 2×2 average pooling. Lastly, the output is a regression layer with one output node.

TABLE 1 detailed architecture of neural network

| Units | Output Size | Layer details |
| --- | --- | --- |
| Convolutional unit | 256 × 256 | 7 × 7 conv, stride 2 |
|  | 128 × 128 | 3 × 3 max pool, stride 2 |
| Block 1 | 128 × 128 | $\begin{bmatrix} 1\times 1\ conv \\ 3\times 3\ conv \end{bmatrix} \times 18$ |
| Transition Unit | 128 × 128 | 1 × 1 conv |
|  | 64 × 64 | 2 × 2 average pool, stride 2 |
| Block 2 | 64 × 64 | $\begin{bmatrix} 1\times 1\ conv \\ 3\times 3\ conv \end{bmatrix} \times 36$ |
| Transition Unit | 64 × 64 | 1 × 1 conv |
|  | 32 × 32 | 2 × 2 average pool, stride 2 |
| Block 3 | 32 × 32 | $\begin{bmatrix} 1\times 1\ conv \\ 3\times 3\ conv \end{bmatrix} \times 36$ |
| Transition Unit | 32 × 32 | 1 × 1 conv |
|  | 16 × 16 | 2 × 2 average pool, stride 2 |
| Block 4 | 16 × 16 | $\begin{bmatrix} 1\times 1\ conv \\ 3\times 3\ conv \end{bmatrix} \times 36$ |
| Transition Unit | 16 × 16 | 1 × 1 conv |
|  | 8 × 8 | 2 × 2 average pool, stride 2 |
| Block 5 | 8 × 8 | $\begin{bmatrix} 1\times 1\ conv \\ 3\times 3\ conv \end{bmatrix} \times 24$ |
| Fully Connected Unit | 1 × 1 | 8 × 8 global average pool |
|  |  | 744 D fully-connected |

Figure 2:
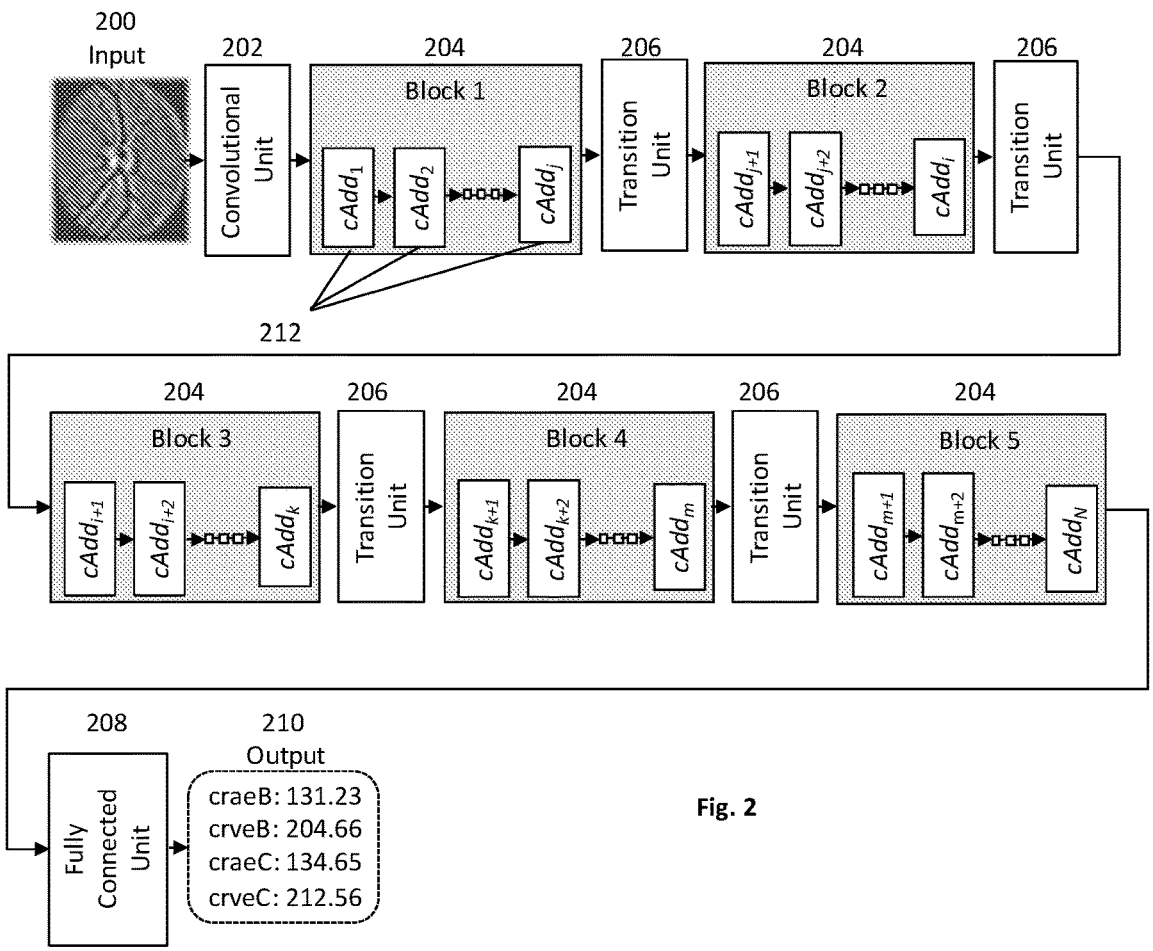
FIG. 2 illustrates a neural network for use in the present methods.

This architecture is illustrated in flow in FIG. 2, wherein, in use, the cropped retina image 200 is passed to convolution unit 202, followed by dense blocks 204 that alternate with transition layers 206 (the last dense block may not be followed by a transition unit), followed by a fully connected unit 208 that outputs vessel caliber (outputs 210). Each dense block comprises a series of cAdd units 212 packed with two types of convolutions as specified in Table 1. The output size progressively decreases through the transition units, and the output of the fully connected unit is 1×1.

To propagate error through the neural network, any suitable error function may be used. Presently, the mean absolute error is used as the loss function.

The models are then trained using stochastic gradient descent with nesterov momentum of 0.9 without dampening and a weight decay of 10-4. During testing a batch size of 80 was used, with a cosine-shaped learning rate and a dropout ratio of 0.2.

Recent deep neural networks (DNN) utilize identity mappings involving either element-wise addition (eAdd) or channelwise concatenation (cCon) for the propagation of these identity mappings. Unlike cCon, cAdd is able to eliminate the need to store feature maps, thus reducing the memory requirement.

As described with reference to FIGS. 6 and 7, the proposed cAdd mechanism is compatible with convolutional neural architectures more generally, and can deepen and widen the neural architectures with fewer parameters compared to cCon and eAdd. To illustrate, cAdd has been incorporated into current state-of-the-art architectures such as ResNet, WideRes-Net, and CondenseNet and, as discussed below, experiments on CIFAR-10, CIFAR-100, and SVHN were carried out to demonstrate that cAdd-based architectures are able to achieve much higher accuracy with much fewer parameters compared to their corresponding base architectures.

Notably, a deeper and wider neural network often yields better performance. However, a deep and wide network suffers from the problem of vanishing gradient as well as a quadratic growth in the number of parameters. Further, the computational complexity and memory requirements also escalate in these architectures which make scalable learning in real world applications harder to achieve.

The depth of a neural architecture is key to its performance. Current neural architectures use identity mappings in the form of skip connections to increase their depth. This allows the gradient to be passed backwards directly thus allowing the increase in depth without the issue of vanishing gradients. The propagation of these identity mappings from one block to the next is achieved either via eAdd or cCon as mentioned above.

Figure 3:
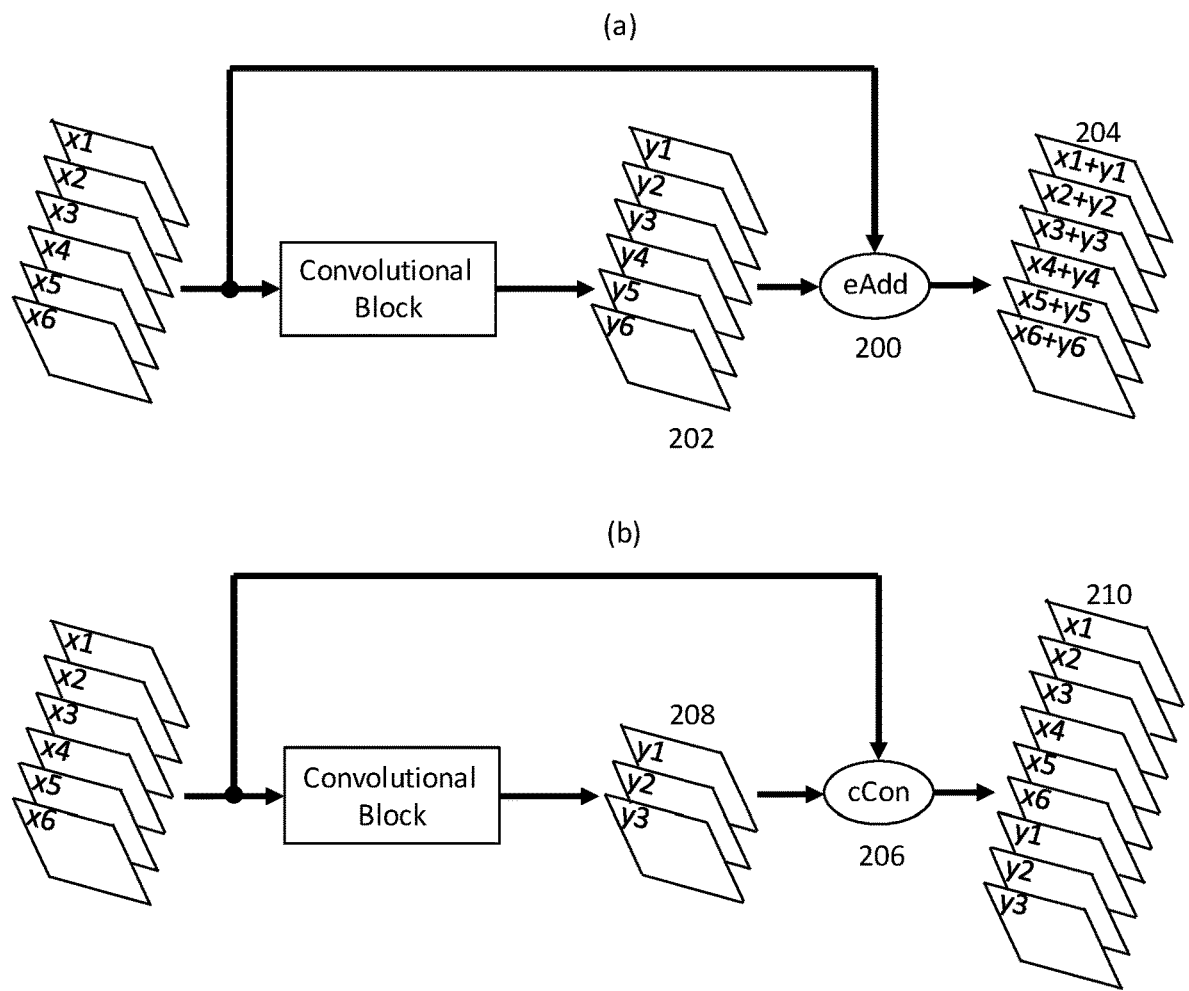
FIG. 3 schematically shows the propagation mechanism of element-wise Addition (eAdd) and channel-wise Concatenation (cCon)

FIG. 3 shows eAdd and cCon propagation mechanisms. In eAdd 200, addition is performed on the corresponding elements, hence the input size for each unit remains the same—e.g. six input channels 202 produces six output channels 204. On the other hand, cCon 206 concatenates the inputs 208 from all the preceding units, thus increasing the input size quadratically 210 for each subsequent unit. As a result, cCon can learn more complex features, however, it needs more memory to store the concatenated inputs.

To maintain the feature complexity of, for example, cCon, while conserving memory by making avoiding quadratic increase in input size, cAdd can be easily incorporated into any of the state-of-art neural architectures. As a result, the computational and memory requirements are reduced while achieving high accuracy.

To keep the memory requirement small, small residual parts are sequentially produced and added to part of channels of the identity part in one unit. The unit is repeated multiple times until all the channels are added. With this, the depth of a network is increased and parameters are reduced.

Figure 4:
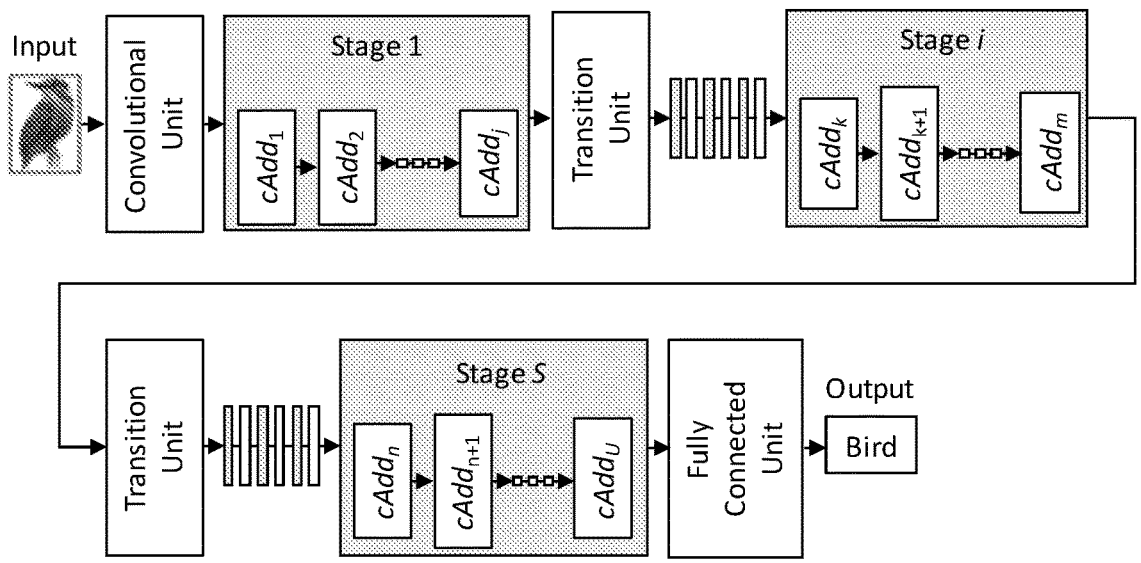
FIG. 4 illustrates the general architecture of a deep neural network using cAdd.

FIG. 4 shows a general architecture 300 of a neural network using cAdd. It has several stages 302, 304, 306 and the cAdd units within each stage have the same resolution for both input and output feature maps—this allows for channel-wise addition. In some embodiments, the resolution across the stages may vary—this will enable down-sampling by transition units.

This cAdd design has several advantages. cAdd provides a shortcut that allows the gradient to bypass a unit directly. This alleviates the vanishing gradient. cAdd adds back the output features instead of concatenation. As a result, the input is kept at the same size for each unit and less memory is needed. More complex features also can be generated as cAdd significantly increases the width and depth of convolutional neural networks (CNNs). Moreover, fewer parameters are needed when compared with existing neural networks with the same width and height.

These advantages were verified by experimental results on the CIFAR-10, CIFAR-100 and SVHN that demonstrate the effectiveness of the proposed propagation mechanism. As discussed with reference to FIGS. 8 to 12, the cAdd-based neural networks consistently achieve higher accuracy with fewer parameters compared to their counterpart networks.

Regarding neural networks using eAdd propagation mechanism, depth is vital for eAdd-based neural networks to achieve higher performance. However, it is hard to optimize deep neural networks. eAdd was introduced in ResNet to significantly deepen the neural network and also ease the training process. It has been widely used in many deep neural networks, including Inception-ResNet, Wide-ResNet, ResNeXt, PyramidNet, Shake-ShakeNet, and ShuffleNets. It is also adopted by AlphaGo and the automatically designed architectures, like NASNet, ENAS, and AmoebaNets.

The width of a neural network is also crucial to gain accuracy. Unlike ResNet, which achieves higher performance by simply stacking element-wise addition, Wide-ResNet widens the network by increasing the input channels along the depth. Experimental results show a 16-layer Wide-ResNet can outperform a thousand-layer ResNet in both accuracy and efficiency. For Wide-ResNet, the increase in width occurs only between stages, and the input size within a stage remains the same. PyramidNet gradually increases its width in a pyramid-like shape with a widening step factor, which has been experimentally proven to improve generalization ability. ResNext uses multi-branch element-wise additions, by replacing the only branch with a set of small homogeneous branches. Simply adding more branches can improve the performance of ResNext. Instead of directly summing up all the small branches, Shakeshake Net uses a stochastic affine combination to significantly improve the generalization ability.

Unlike the manual designs, that require human expertise, the automatically designed architectures search the entire architecture space to find the best design. Although the learned architectures have many different small branches, the distinct characteristic is that they all use eAdd to sum up the branches.

Since the eAdd requires the output size to be at least the same or larger than the input size, a neural network can go deeper or wider, but not both when the number of parameters is limited. There is therefore a trade-off between neural network width and depth.

Regarding neural networks that use cCon, such as DenseNet, features from all preceding units are used as inputs to generate a small number of outputs, which are passed to subsequent units. While this strengthens feature propagation and reuse, it is not necessary for all prior features to be used as inputs to every subsequent layer.

CondenseNet selects only the most relevant inputs through a learned group convolution. It sparsifies the convolutional layer by pruning away unimportant filters during the condensing stage, and optimizes the sparsified model in the second half of the training process. As pruning the superfluous filters, CondenseNet is more efficient than the compact MobileNes and ShuffleNets, which are especially designed for mobile devices using depth-wise separable convolutions.

For the automatically designed architectures, cCon is fully used in their most accurate models, especially for the combination of all the cell outputs. However, since concatenation increases the input size linearly, this also increases the number of parameters and memory requirements. In contrast, the proposed cAdd is able to keep the input size constant by adding back outputs to selected inputs. Moreover, eAdd enables a neural network to be deepened or widened, but not both. In contrast, cAdd can both deepen and widen a neural network for the same number of parameters.

Figure 5:
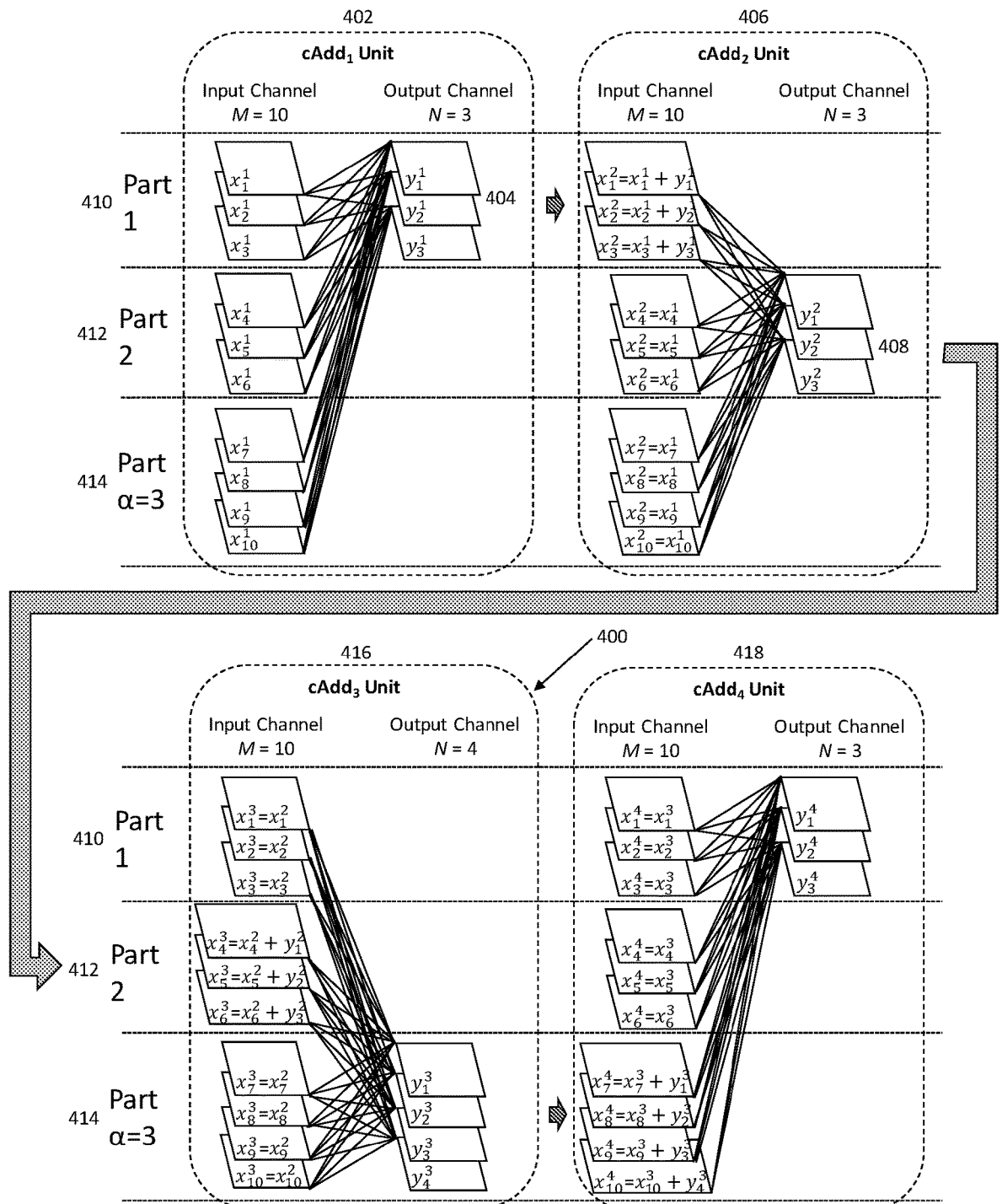
FIG. 5 shows an example of a propagation mechanism within a cAdd stage comprising four cAdd units.

As a result, cAdd combines the benefits of the eAdd and cCon propagation mechanisms to deepen and widen the networks with fewer parameters. FIG. 5 shows the propagation of one cAdd stage 400 across four units using cAdd. Each unit must generate a small number of output channels whereby the generated outputs are then added back to corresponding skipped connections to form as inputs to the next unit. In the example shown in FIG. 5, the first cAdd unit 402 generates outputs 404 that are then added as inputs for skipped connection of a subsequent cAdd unit 406. In particular, cAdd unit 402 generates three outputs 404. The three outputs 404 are then added back to the first three skipped connections 408 (i.e. skipped by cAdd 402) to form the inputs to the second cAdd unit 406.

Suppose M is the number of input channels. To ensure all the skipped connections are covered, the input channels of each unit are grouped into non-overlapping parts or groups. For each cAdd unit, outputs of all input channels are added to one of the non-overlapping groups, wherein, for successive cAdd units, the output group is a different one of said non-overlapping groups.

The size of each part (i.e. non-overlapping group) is controlled by a parameter α such that each part 410, 412 has exactly $\lfloor M/\alpha \rfloor$ channels except the final part 414 which has $\lfloor M/\alpha \rfloor + R$ channels where R is the remaining channels. With further reference to FIG. 5, the second input part 412 has $\lfloor M/\alpha \rfloor = 3$ channels. These channels are covered by the addition to the outputs of the cAdd$_2$ unit 406. The third and final input part 414 has $\lfloor M/\alpha \rfloor + R = 4$ channels that are skipped in cAdd 402 and cAdd 404, and are covered by the addition to the outputs of the cAdd$_3$ unit 416. As a result, each cAdd unit skips all but one of the non-overlapping groups, and each non-overlapping group that is skipped in one cAdd unit is connected in at least one other cAdd unit. In fact, in the example shown in FIG. 5, of the α non-overlapping groups 410, 412, 414, and α+1 cAdd units 402, 406, 416, 418 in each cAdd stage 400, each non-overlapping group is connected in exactly one cAdd unit, except for one non-overlapping group 414, which is connected in the first cAdd unit 402 that receives the input channels to the cAdd stage 400, and a second cAdd unit 418 that provides the outputs from the cAdd stage 400.

In order for the addition operation to make sense, the number of generated outputs from a unit must match the number of channels to be covered in the next unit. Mathematically, the number of output channels for the $k^{th}$ cAdd unit is given by:

$$\begin{cases} \lfloor M/\alpha \rfloor, & k \% \alpha \neq 0 \\ \lfloor M/\alpha \rfloor + M \% \alpha, & \text{otherwise} \end{cases} \quad (1)$$

To analyse the propagation mechanism, let $X = [x_1, x_2, \ldots, x_M]$ be the input to a cAdd unit, and $Y = [y_1, y_2, \ldots, y_N]$ be the output of X after passing through the non-linear transformation function $F(\bullet)$ of the convolutional block, which may have different layers consisting of batch normalization (BN), rectified linear units (ReLU), and convolution layers (Conv). That is, $$Y = \mathcal{F}(X) \quad (2)$$

The cAdd unit adds back its outputs Y into part of its inputs X to form the inputs X' for the next unit as follows:

$$X' = X + TY \quad (3)$$

where T is a M×N sparse matrix, $T_{ij} = 1$ if $y_j$ is to be added to $x_i$.

From Equations 2 and 3:

$$X' = X + T \cdot \mathcal{F}(X) \quad (4)$$

Now consider the propagation from cAdd unit s to cAdd unit e whose corresponding inputs are $X^S$ and $X^e$ respectively. This produces:

$$X^e = X^s + \sum_{i=s}^{e-1} T^i \cdot \mathcal{F}(X^i) \quad (5)$$

Let E be the error loss. The gradient on $X^s$ can then be expressed as:

$$\frac{\partial E}{\partial X^s} = \frac{\partial E}{\partial X^e} \frac{\partial X^e}{\partial X^s} = \frac{\partial E}{\partial X^e}\left(1 + \sum_{i=s}^{e-1} T^i \cdot \frac{\partial \mathcal{F}(X^i)}{\partial X^s}\right) \quad (6)$$

It is not possible for all the training samples within a batch to have the component in Equation (6) always equal to −1. This therefore shows that the cAdd propagation mechanism is able to alleviate the vanishing gradient problem.

To analyse the parameters, the pre-determined parameter α is used to control the complexity of each cAdd unit. A large α will imply a significant reduction in the number of output channels, leading to a decrease in the number of parameters of a neural network. It is therefore important to analyse the number of parameters in a neural architecture using cAdd.

Figure 6:
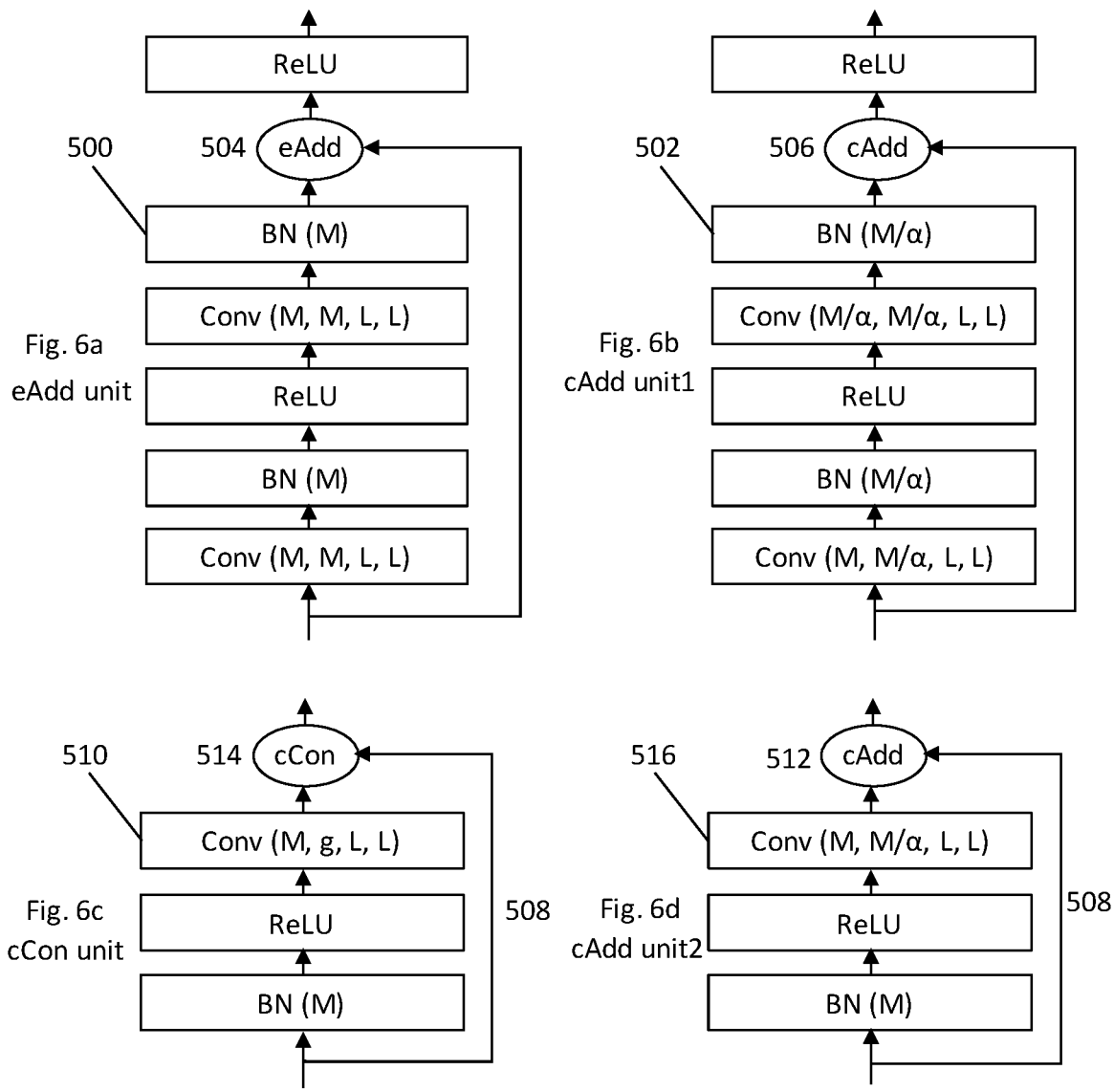
FIG. 6 shows the portability of cAdd into existing architectures, by substitution for different propagation mechanisms.

FIG. 6, comprising FIGS. 6(a) to (d), shows the basic units of a neural architecture using different propagation mechanisms. The notations are:

Conv(I, O, L, L). Convolution layer with I input channels, O output channels, and kernel size L×L.

BN(I). Batch normalization with I input channels.

ReLU. Rectified linear unit.

In these examples, a simple substitution has been applied, where in FIGS. 6(a) and 56b), outputs of batch normalisation layer 500, 502 are fed to eAdd 504 and cAdd 506 respectively, and each takes the same input channels. Similarly, in FIGS. 6(c) and 6(d) the input channels 508 and convolutional layer outputs 510, 516 can be fed to cAdd 512 the same way as for cCon 514. In each case, the non-overlapping groups are propagated through the network.

For fair comparison, it is assumed that the growth rate g for a cCon unit is M/a so that the cCon unit has the same number of outputs as cAdd. Table 2 gives the number of parameters required for a neural network with M input channels and U basic units.

TABLE 2

Comparison of parameters required.

| Basic Unit | Number of Parameters |
|---|---|
| cAdd unit | $2 * U * M^2 * L^2$ |
| cAdd unit1 | $U * M^2 * L^2 * (1/\alpha + 1/\alpha^2)$ |
| cCon unit | $U * M^2/\alpha * L^2 + (M/\alpha)^2 * L^2 *(U^2 - U)/2$ |
| cAdd unit2 | $U * M^2/\alpha * L^2$ |

A neural network using cAdd has approximately 2α times fewer parameters compared to a network that uses eAdd. That is, with the same number of parameters, the depth of a neural network using cAdd can be increased by 2α, or the width can be increased by $\sqrt{2\alpha}$ compared to using eAdd.

Such an increase can improve the generalization ability of the neural networks, thus leading to higher accuracy.

The number of parameters required by cCon in Table 2 is greater than cAdd. The residual part of $(M/\alpha)^2 * L^2 * (U^2 - U)/2$ is introduced by concatenation operation.

In addition to the ability to widen and deepen networks using cAdd when compared with eAdd, and to reduce parameter requirements when compared with cCon, a cAdd unit can be easily incorporated into existing neural networks, by replacing their corresponding eAdd and/or cCon units.

For neural networks using eAdd, there are two kinds of units, basic and bottleneck units. In the eAdd basic unit, the number of output channels must be the same as that of the input channels for element-wise addition. This is no longer the case when we replace eAdd by cAdd. Under cAdd operation, the number of output channels, O, is determined based on Equation 1. In other words, we simply change the initial convolution layer of eAdd's basic unit from Conv(M, M, L, L) to Conv(M, O, L, L), O<<M, for cAdd.

The eAdd's bottleneck unit uses convolution layer with kernel size 1×1 to spatially combine large numbers of input feature maps with few parameters (see bottleneck unit 600 of FIG. 7(*a*)). Due to the element-wise addition requirement 602, an additional convolution layer 604 is needed to expand the size of the output channels back to M. However, this is not needed for channel-wise addition. FIG. 7(*b*) shows the modified cAdd bottleneck unit 606 with cAdd 608. Similar adaptations can be applied to variants such as pre-activation and those used in PyramidNet.

Adapting cCon-based neural networks to use cAdd is straightforward whereby the number of output channels for both the basic and bottleneck units is determined using Equation 1 instead of by the growth rate.

The effectiveness of cAdd was experimentally compared with eAdd and cCon. Three widely used CNN architectures, ResNet, WRN and CondenseNet, were adapted to use cAdd as described in the previous section. The adapted architectures are referred to as cResNet, cWRN and cCondenseNet respectively. Each architecture has 3 stages.

The networks were trained using stochastic gradient descent with nesterov momentum of 0.9 without dampening, and a weight decay of $10^{-4}$. For fair comparison, all the training settings (learning rate, batch size, epochs, and data augmentations) are the same as in the original papers, unless otherwise specified. The following datasets are used:

CIFAR-10: It has 10 object classes with 6,000 32×32 color images for each class. There are 50,000 images for tanning and 10,000 for testing.

CIFAR-100: It has 100 classes with 600 32×32 color images for each class. The training and testing sets contain 50,000 and 10,000 images respectively.

SVHN: This has over 600,000 32×32 images of real-world house numbers. There are 73,257 images for training, 26,032 for testing, and additional 531,131 for extra training.

In this set of experiments, the performance of ResNet with cResNet was examined. Like ResNet, all the cResNet ($\alpha$=7) were trained for 300 epochs with batch size of 128. The learning rate starts from 0.1 and is reduced by 10 after the $150^{th}$ and $225^{th}$ epoch. For the 1224-layer cResNet, the initial learning rate is 0.01 for the first 20 epochs, and then reverts to 0.1 to continue the training.

Table 3 gives the results of ResNet, pre-activation ResNet, and cResNet on CIFAR-10, CIFAR-100, and SVHN datasets. ResNet-20 with 0.27 million parameters has a depth of 20, and its widths for three stages are 16, 32, and 64 respectively. In contrast, cResNet-86 with comparable number of parameters (0.21 million) has a depth of 86, and its corresponding widths are 84, 112, and 140. The increased width and depth in cResNet-86 over ResNet-20 enables it to have a much higher accuracy on CIFAR-10. In fact, the accuracy of cResNet-86 beats ResNet-56 on CIFAR-10, CIFAR-100 and SVHN datasets, which have four times the number of parameters.

TABLE 3

Top-1 error rate of ResNet and cResNet. Width is the number of input channels in the three stages. * and + indicates the the results are from accepted references. Results for cResNet are averaged over 5 runs in the format of "mean ± std".

| Architecture | Width | # Params | CIFAR-10 | CIFAR-100 | SVHN |
| --- | --- | --- | --- | --- | --- |
| ResNet-20 [7] | 16-32-64 | 0.27M | 8.75 | — | — |
| ResNet-32 [7] | 16-32-64 | 0.46M | 7.51 | — | — |
| ResNet-44 [7] | 16-32-64 | 0.66M | 7.17 | — | — |
| ResNet-56 [7] | 16-32-64 | 0.85M | 6.97 | 28.25 * | 2.49 * |
| ResNet-110 [7] | 16-32-64 | 1.73M | 6.61 ± 0.16 | 27.22 † | 2.01 † |
| ResNet-164 [7] | 16-32-64 | 1.70M | — | 25.16 | — |
| ResNet-1001 [7] | 16-32-64 | 10.2M | — | 27.82 | — |
| ResNet-1202 [7] | 16-32-64 | 19.4M | 7.93 | — | — |
| Pre-activation ResNet -164 [8] | 64-128-256 | 1.7M | 5.46 | 24.33 | — |
| Pre-activation ResNet - 1001 [8] | 64-128-256 | 10.2M | 4.92 | 22.71 | — |
| cResNet-86 | 84-112-140 | 0.21M | 6.37 ± 0.09 | 27.45 ± 0.11 | 2.09 ± 0.07 |
| cResNet-86 | 168-196-308 | 0.84M | 4.76 ± 0.07 | 23.35 ± 0.17 | 2.04 ± 0.07 |
| cResNet-170 | 196-224-280 | 1.65M | 4.33 ± 0.04 | 21.33 ± 0.20 | 1.92 ± 0.06 |
| cResNet-1224 | 196-224-280 | 13.185M | 4.06 | — | — |

When the width of cResNet-86 was increased to 168-196-308 so that it has a comparable number of parameters (0.84 million) as ResNet-56, the gap in accuracy widens significantly. In the experiments, cResNet-86 also outperformed ResNet-110, ResNet-164 and pre-activation ResNet-164, which have twice the number of parameters. It is seen that cResNet-170 with 1.65 million parameters gives the best results over all the ResNets and pre-activation ResNets.

FIG. 8 shows the top-1 error rates of the cResNet and ResNet on CIFAR-10 dataset as the number of parameters is varied. Clearly, the error rate of cResNet is always lower than ResNet for the same number of parameters. The graph of FIG. 8 also shows that ResNet at its lowest error rate has 8 times more parameters than cResNet.

Another advantage that cAdd has over eAdd is its ability to reduce over-fitting. ResNet-1202 has 19.4 million parameters, and its error rate is higher than ResNet-110 due to over-fitting.

Figure 9:
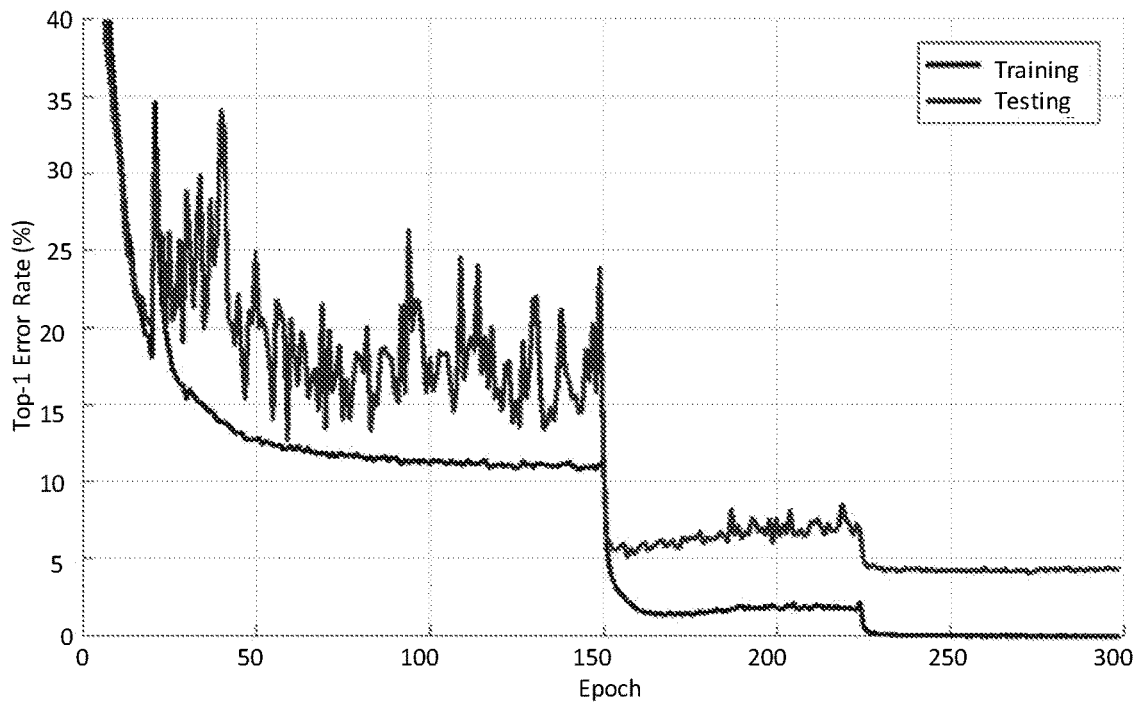
FIG. 9 shows training and testing curves of cResNet-1224.

On the other hand, cResNet-1224, which is much wider and deeper than ResNet-1202, achieves the lowest top-1 error rate of 4.06 on CIFAR-10 (see Table 3) over-fitting as demonstrated by its training and testing curves in FIG. 9.

The performance of WRN with cWRN was also checked experimentally. Similar to WRN, cWRN ($\alpha=7$) was trained for 200 epochs with batch size of 128. The learning rate starts from 0.1, annealed by a factor of 5 times after the $60^{th}$, $120^{th}$, and $160^{th}$ epochs for CIFAR-10 and CIFAR-100 datasets. For SVHN dataset, cWRN are trained for 160 epochs with batch size of 128, and is optimized by dividing the initial learning rate of 0.01 by 10 after the $80^{th}$ and $120^{th}$ epochs.

Table 4 gives the results. All the cWRN are much wider and deeper compared to the corresponding WRN, and are able to achieve lower top-1 error rates with fewer parameters on all three datasets. Specifically, cWRN-130-2 outperforms WRN-52-1 with half the parameters (0.39 million vs. 0.76 million) on all three datasets. Overall, cWRN-88-13 gives the best performance.

TABLE 4

Top-1 error rate of WRN and cWRN. Width is the number of input channels in the three stages. Results for cWRN are averaged over 5 runs in the format of "mean ± std".

| Architecture | Width | # Params | CIFAR-10 | CIFAR-100 | SVHN |
| --- | --- | --- | --- | --- | --- |
| WRN-52-1 [32] | 16-32-64 | 0.76M | 6.43 | 28.89 | 2.08 |
| WRN-16-4 [32] | 64-128-256 | 2.75M | 5.02 | 24.03 | 1.85 |
| WRN-40-4 [32] | 64-128-256 | 8.95M | 4.53 | 21.18 | — |
| WRN-16-8 [32] | 128-256-512 | 11.00M | 4.27 | 20.43 | — |
| cWRN-130-2 | 98-126-154 | 0.39M | 6.32 ± 0.10 | 26.75 ± 0.20 | 1.99 ± 0.06 |
| cWRN-130-4 | 196-252-308 | 1.52M | 4.87 ± 0.09 | 22.4 ± 0.19 | 1.81 ± 0.05 |
| cWRN-172-6 | 294-378-462 | 4.41M | 4.34 ± 0.09 | 20.87 ± 0.13 | — |
| cWRN-172-8 | 392-504-616 | 7.80M | 4.26 ± 0.07 | 19.78 ± 0.17 | — |
| cWRN-88-13 | 637-819-1001 | 10.90M | 4.04 ± 0.09 | 19.33 ± 0.13 | — |

Figure 10:
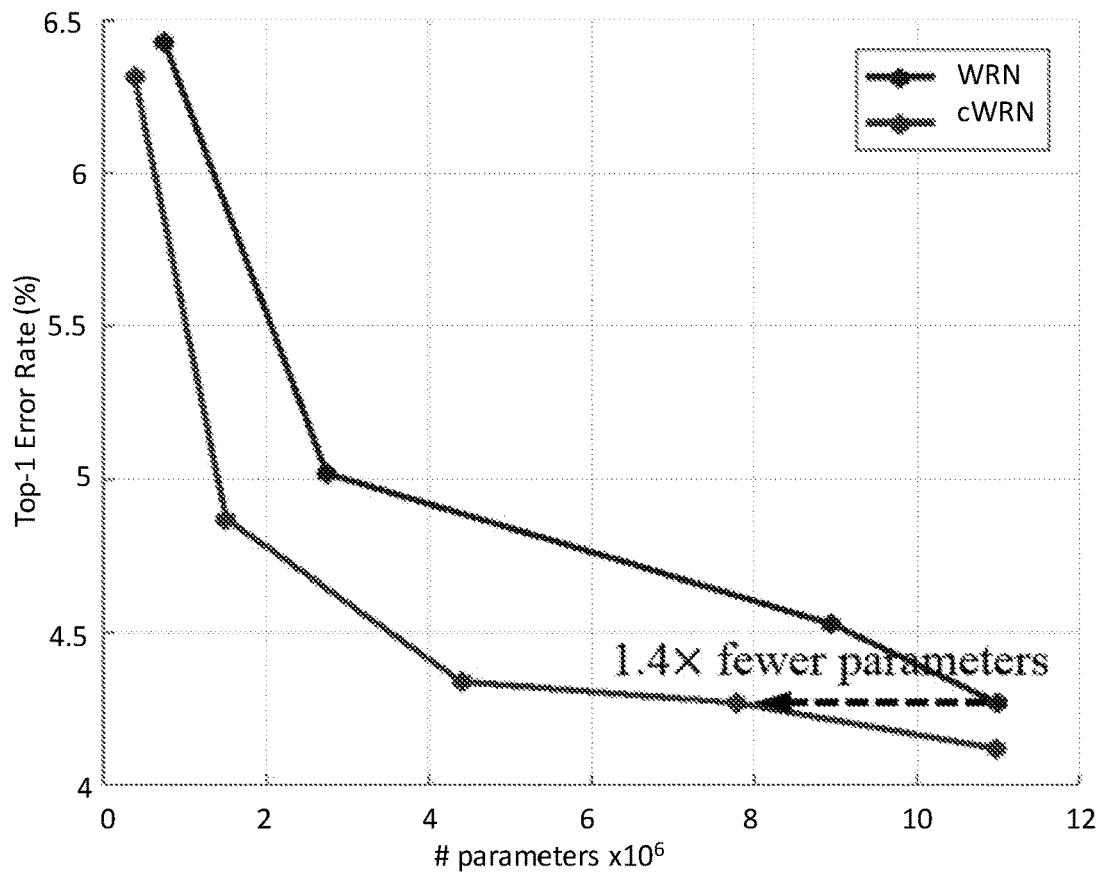
FIG. 10 shows training curves of Wide-ResNet (WRN) and cWRN on CIFAR-10.

FIG. 10 shows the top-1 error rates of the cWRN and WRN on CIFAR-10 dataset as the number of parameters. cWRN is shown to have 1.4 times fewer parameters than WRN for the same error rate.

Finally, the performance of cAdd in CondenseNet was examined. All the cCondenseNet ($\alpha=6$) were trained for 300 epochs with a batch size of 64, and used a cosine-shaped learning rate from 0.1 to 0. cCondenseNet-254 was trained for 600 epochs with a dropout rate of 0.1 to ensure fair comparison with CondenseNet-182.

Table 5 shows the results with cCondenseNet-254 giving the best performance on both CIFAR-10 and CIFAR-100. It has 456 input channels which is 38 times the width of CondenseNet-182, and 254 convolutional layers which is 1.4 times the depth of CondenseNet-182. cCondenseNet-146 and cCondenseNet-110 are clearly much wider and deeper with fewer parameters compared to their counterparts CondenseNet-86 and CondenseNet-50. In particular, although cCondenseNet-110 has 0.03 million fewer parameters than CondenseNet-50, its top-1 error rate is smaller than that of CondenseNet-50, 5.74 versus 6.22.

TABLE 5

Top-1 error rate of CondenseNet and cCondenseNet. Width is the number of input channels or growth rate in the three stages. Results for cCondenseNet are averaged over 5 runs in the format of "mean ± std".

| Architecture | Width | # Params | CIFAR-10 | CIFAR-100 |
| --- | --- | --- | --- | --- |
| CondenseNet-50 [11] | 8-16-32 | 0.22M | 6.22 | — |
| CondenseNet-74 [11] | 8-16-32 | 0.41M | 5.28 | — |
| CondenseNet-86 [11] | 8-16-32 | 0.52M | 5.06 | 23.64 |
| CondenseNet-98 [11] | 8-16-32 | 0.65M | 4.83 | — |
| CondenseNet-110 [11] | 8-16-32 | 0.79M | 4.63 | — |
| CondenseNet-122 [11] | 8-16-32 | 0.95M | 4.48 | — |
| CondenseNet-182 [11] | 12-24-48 | 4.22M | 3.76 | 18.47 |

TABLE 5-continued

Top-1 error rate of CondenseNet and cCondenseNet. Width is the number of input channels or growth rate in the three stages. Results for cCondenseNet are averaged over 5 runs in the format of "mean ± std".

| Architecture | Width | # Params | CIFAR-10 | CIFAR-100 |
|---|---|---|---|---|
| cCondenseNet-110 | 96-144-192 | 0.19M | 5.74 ± 0.08 | 27.40 ± 0.15 |
| cCondenseNet-146 | 168-216-264 | 0.50M | 4.64 ± 0.08 | 23.44 ± 0.11 |
| cCondenseNet-254 | 456-504-576 | 4.16M | 3.40 ± 0.09 | 18.20 ± 0.13 |

Figure 11:
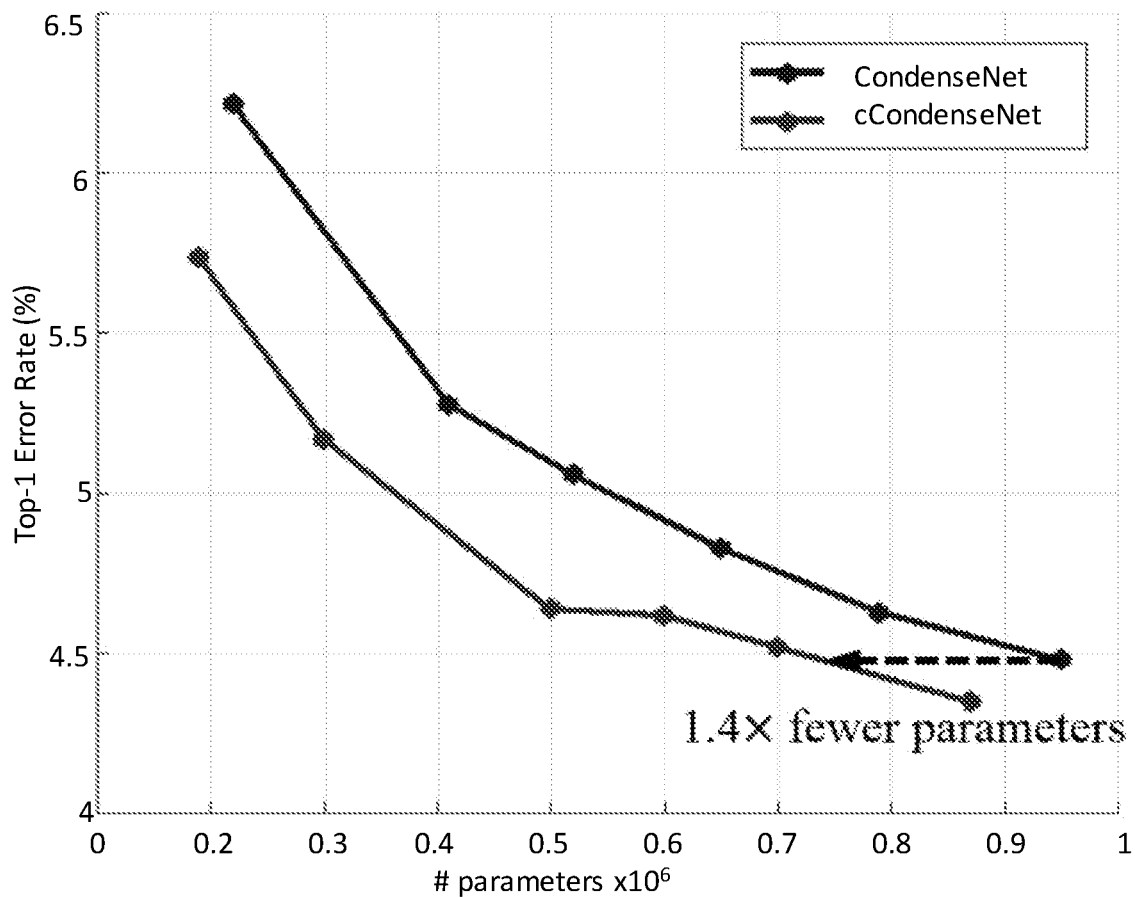
FIG. 11 shows training curves of CondenseNet vs. cCondenseNet on CIFAR-10.

FIG. 11 compares the top-1 error rates on CIFAR-10. Clearly, cCondenseNet has 1.4 times fewer parameters than CondenseNet for the same error rate.

Figure 12A:
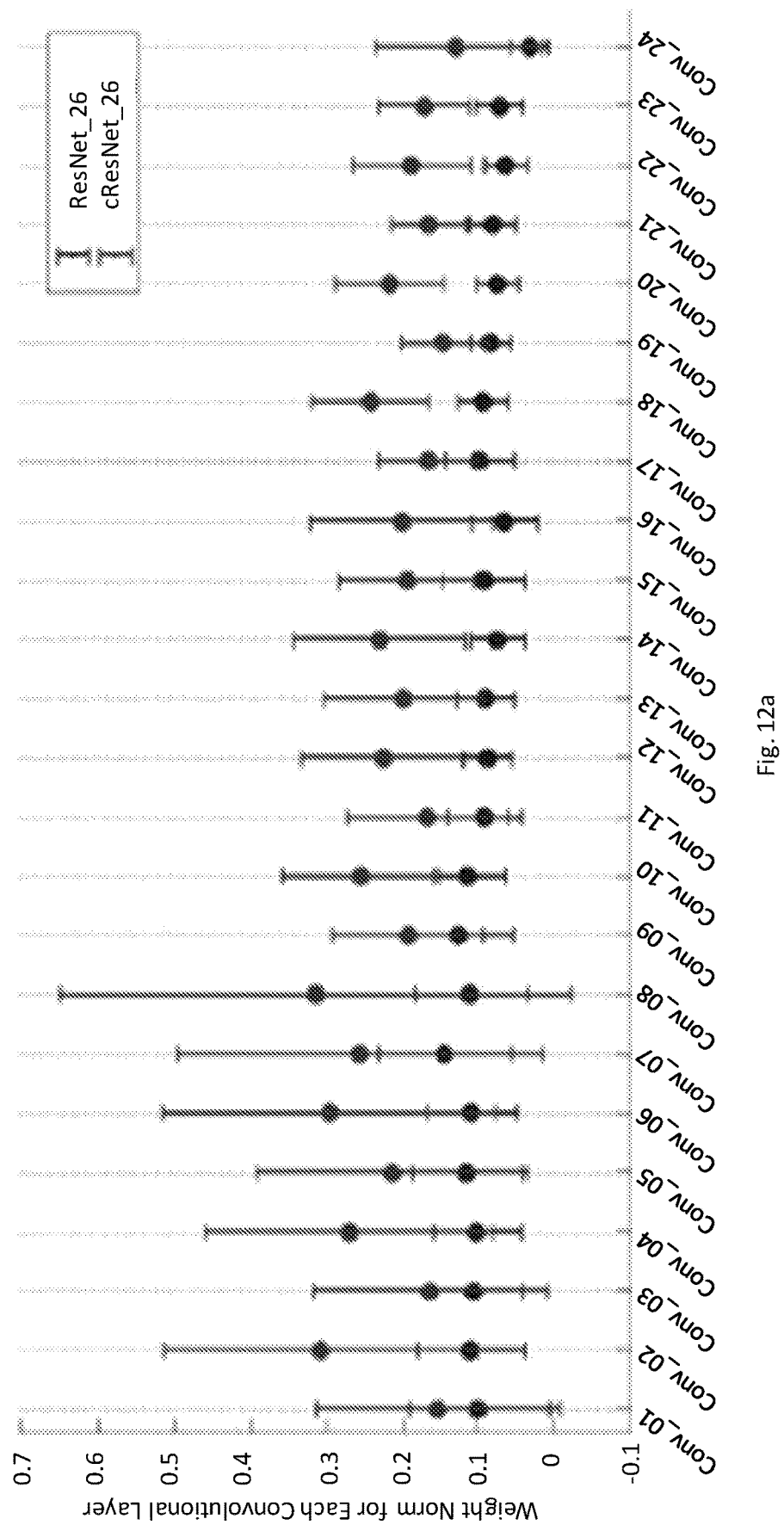
FIG. 12 shows the neuron weights in the convolutional layer of architecturess using cAdd, eAdd and cCon.
Figure 12B:
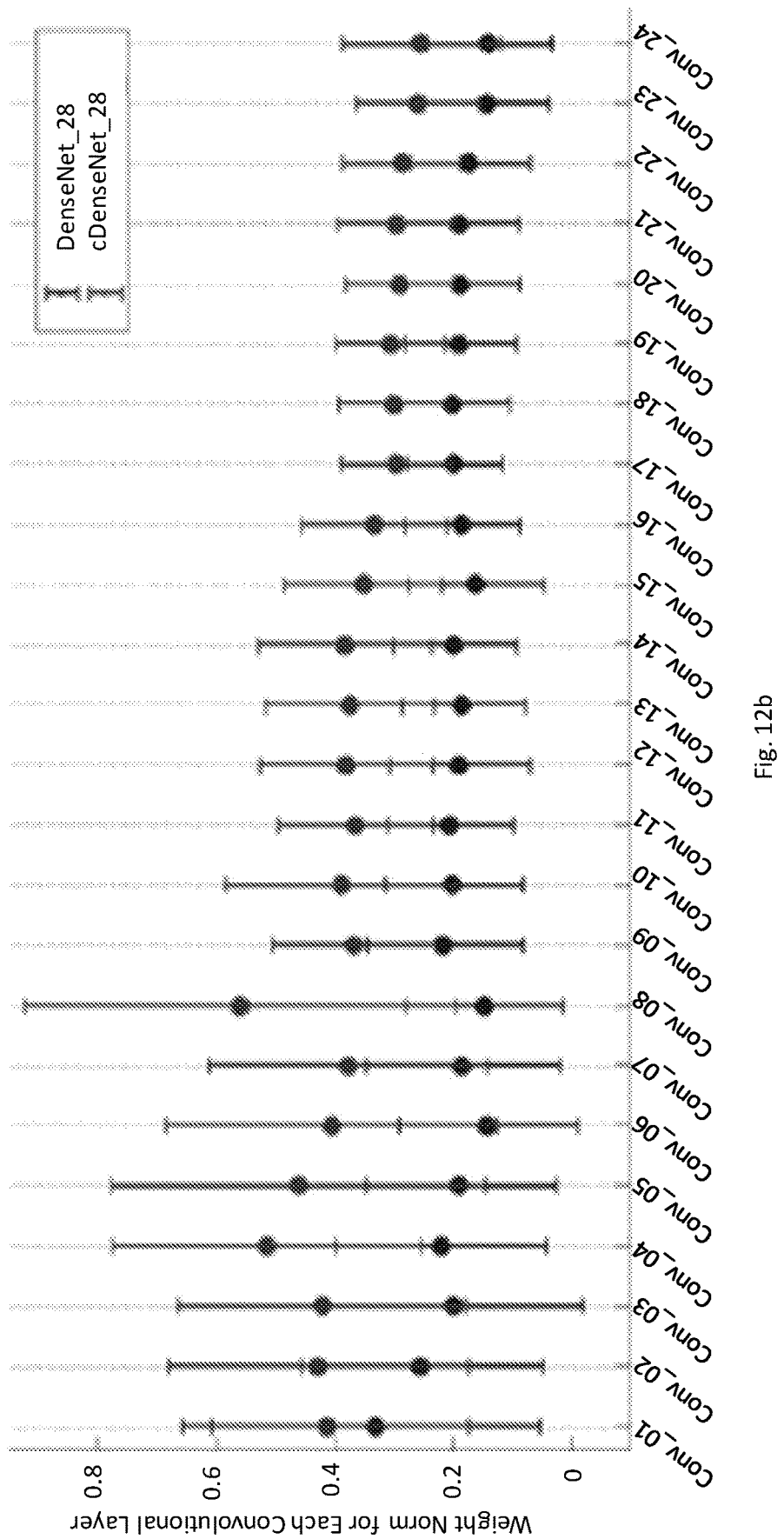

To determine what is happening in the neural network, weight norm can be used to measure the activeness of neurons during feature learning. FIG. 12 shows the mean and standard deviation of the neuron weights within each convolutional layer of the trained neural networks using cAdd (adapted from ResNet-26 and DenseNet-28), eAdd (ResNet-26), and cCon (DenseNet-28). As shown, the neurons in the cAdd based network have larger weights than eAdd and cCon based networks. This indicates that cAdd neurons are more active compared to eAdd and cCon neurons during feature learning. This may be due to eAdd and cCon introducing a substantial number of learning weights, many of which are close to zero and can be pruned without sacrificing accuracy. With cAdd, the number of weights can be reduced, leading to fewer parameters as set out in Table 2, and higher accuracy as shown in Tables 3 to 5.

As discussed with reference to FIGS. 3 to 6, depth and width are vital dimensions for neural networks to achieve higher performance. Depth controls the complexity of the learned features. A deeper neural network can learn more complex features, while a wider network enables more features to be involved in the final classification.

For cAdd based architectures, we have the flexibility of either increasing the depth or the width or both and still retain approximately the same number of parameters. It is useful therefore to investigate the impact of the depth and width of a cAdd based architecture on its classification accuracy. To do this, ResNet-56 with 0.85 million parameters, and CondenseNet-86 with 0.52 million parameters were used as the baselines, and different cResNet and cCondenseNet were designed with approximately the same number of parameters at varying depth and width. Table 6 shows the results on both CIFAR-10 and CIFAR-100 datasets.

TABLE 6

Top-1 error rate of cResNet, and cCondenseNet on CIFAR-10, and CIFAR-100 datasets.

| Architecture | # Params | Width | Depth | CIFAR-10 | CIFAR-100 |
|---|---|---|---|---|---|
| ResNet-56 [7] (Base-line) | 0.85M | 16-32-64 | 56 | 6.97 | 28.25 |
| cResNet-44 | 086M | 280-308-336 | 44 | 6.20 | 27.14 |
| cResNet-86 | 0.81M | 196-224-252 | 86 | 5.91 | 27.09 |
| cResNet-128 | 0.89M | 168-196-224 | 128 | 5.84 | 26.94 |
| cResNet-170 | 0.88M | 140-168-196 | 170 | 5.66 | 27.04 |
| cResNet-212 | 0.89M | 126-154-182 | 212 | 5.50 | 26.93 |
| cResNet-254 | 0.88M | 112-140-168 | 254 | 5.88 | 27.39 |
| cResNet-296 | 0.86M | 100-128-156 | 296 | 5.95 | 27.77 |
| cResNet-338 | 0.82M | 91-119-147 | 338 | 5.94 | 27.55 |
| CondenseNet-86 [11] (Base-line) | 0.52M | 8-16-32 | 86 | 5.06 | 23.64 |
| cCondenseNet-38 | 0.51M | 312-360-384 | 38 | 5.08 | 25.29 |
| cCondenseNet-74 | 0.49M | 240-288-312 | 74 | 4.89 | 24.19 |
| cCondenseNet-110 | 0.51M | 216-240-288 | 110 | 4.73 | 24.02 |
| cCondenseNet-182 | 0.51M | 168-192-240 | 182 | 4.61 | 23.46 |
| cCondenseNet-218 | 0.51M | 144-192-216 | 218 | 4.94 | 23.56 |
| cCondenseNet-254 | 0.49M | 120-168-216 | 254 | 4.89 | 23.74 |
| cCondenseNet-290 | 0.51M | 120-168-192 | 290 | 4.86 | 24.19 |
| cCondenseNet-326 | 0.51M | 120-144-192 | 326 | 5.11 | 24.24 |

As shown in Table 6, the best performances are attained when the increase in depth is balanced with the increase in width, indicating that both depth and width are equally important. This makes sense as the performance of a neural net depends both on the number of features as well as the complexity of these features.

As set out above, a channel-wise addition propagation mechanism can be used to deepen and widen neural networks with significantly fewer parameters, when compared with other propagation mechanisms.

The above can then be used in step 106 to train the multi-layer neural network by passing the pre-processed fundus images to input channels of a cAdd stage, before passing outputs (of the cAdd stage) to a convolution layer of the neural network.

Figure 1:
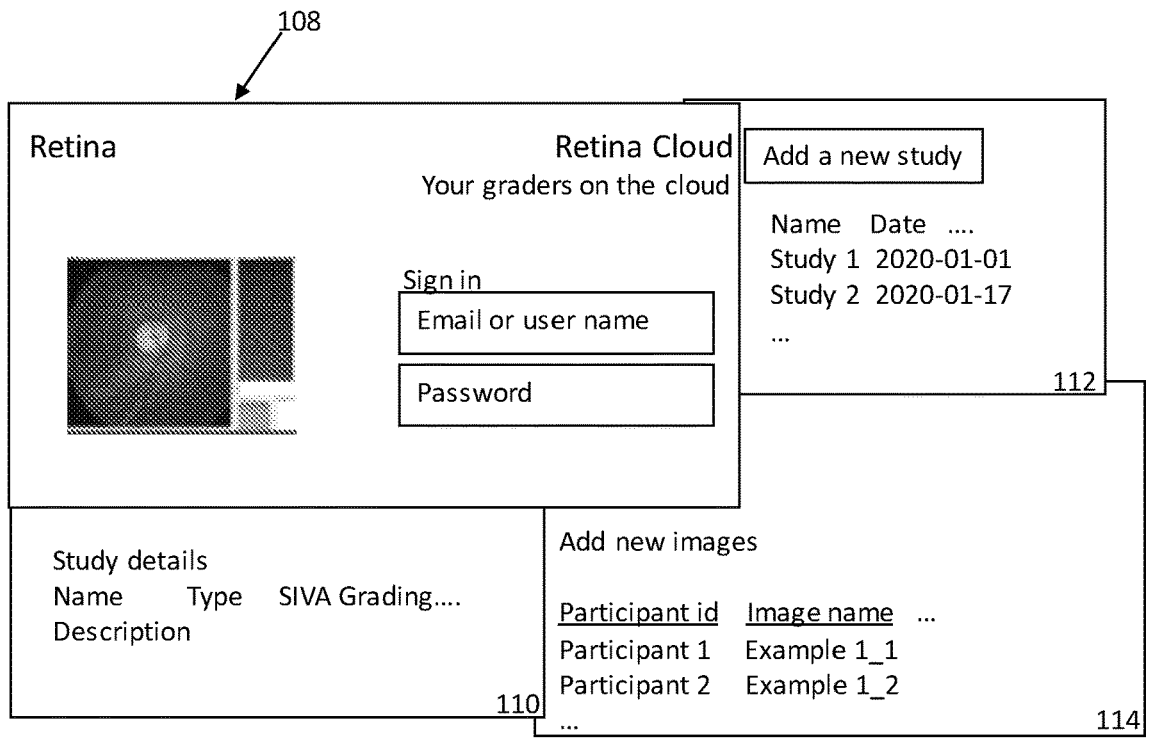
FIG. 1 illustrates a cloud-based interface for interacting with a system according to present teachings, for assessing retina fundus images.

To facilitate access to the system, a cloud-based web system can be used that provides a one-stop interface shown in FIG. 1, allowing users to manage research studies and process digital fundus photographs for the objective assessment of retinal vascular parameters. This platform is designed to cater the needs of all levels of users involved, providing a simple solution for the management of research studies for different teams across the organization.

The cloud-based platform is also accessible from most internet-enabled devices, reducing impacts of use of the system as a result of geographical limitations. FIG. 1 shows the key functions of the platform 108: logged-in users can sign in to the platform via interface 110, and view and modify study details, upload images, generate vessel parameters data through interfaces 112, 114 and 116.

Also provided is a system for performing the method of FIG. 13, and for classifying a fundus image using that method. In this regard, the present method will be understood to be performed, accessed or implemented on such a system—i.e. the system comprises memory and a processor (which may be distributed across multiple servers), the memory comprising instructions that when executed by the processor result in performance of the method. That system may be a stand-alone system or, in a preferred embodiment, is deployed on a cloud platform. A serverless computing model may also be used to build and host the neural network and interfaces for accessing it. This allows the system to be instantaneously scalable without manual intervention.

Figure 14:
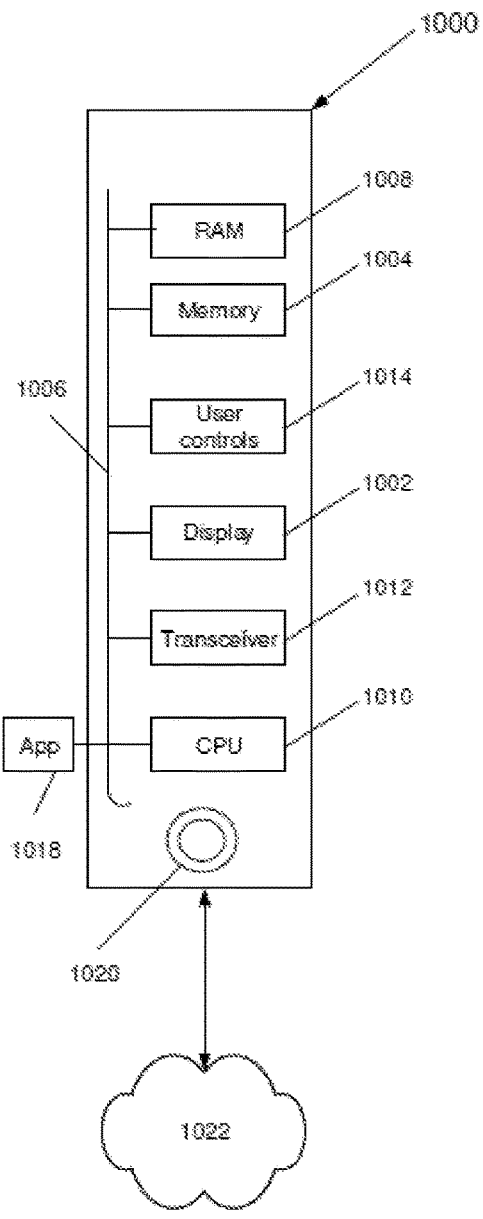
FIG. 14 schematically illustrates a system for performing the method of FIG. 13, or through which a cloud-based platform implementing the method of FIG. 13 can be accessed.

FIG. 14 is a block diagram showing an exemplary mobile computer device 1000 in which embodiments of the invention may be practiced. The mobile computer device 1000 may be a mobile computer device such as a smart phone, a personal data assistant (PDA), a palm-top computer, and multimedia Internet enabled cellular telephones. For ease of description, the mobile computer device 1000 is described below, by way of non-limiting example, with reference to a mobile device in the form of an iPhone™ manufactured by Apple™, Inc., or one manufactured by LG™, HTC™ and Samsung™, for example.

As shown, the mobile computer device 1000 includes the following components in electronic communication via a bus 1006:

(a) a display 1002;
(b) non-volatile (non-transitory) memory 1004;
(c) random access memory ("RAM") 1008;
(d) N processing components 1010;
(e) a transceiver component 1012 that includes N transceivers; and
(f) user controls 1014.

Although the components depicted in FIG. 11 represent physical components, FIG. 11 is not intended to be a hardware diagram. Thus, many of the components depicted in FIG. 11 may be realized by common constructs or distributed among additional physical components. Moreover, it is certainly contemplated that other existing and yet-to-be developed physical components and architectures may be utilized to implement the functional components described with reference to FIG. 11.

The display 1002 generally operates to provide a presentation of content to a user, and may be realized by any of a variety of displays (e.g., CRT, LCD, HDMI, micro-projector and OLED displays).

In general, the non-volatile data storage 1004 (also referred to as non-volatile memory) functions to store (e.g., persistently store) data and executable code.

In some embodiments for example, the non-volatile memory 1004 includes bootloader code, modem software, operating system code, file system code, and code to facilitate the implementation components, well known to those of ordinary skill in the art, which are not depicted nor described for simplicity.

In many implementations, the non-volatile memory 1004 is realized by flash memory (e.g., NAND or ONENAND memory), but it is certainly contemplated that other memory types may be utilized as well. Although it may be possible to execute the code from the non-volatile memory 1004, the executable code in the non-volatile memory 1004 is typically loaded into RAM 1008 and executed by one or more of the N processing components 1010.

The N processing components 1010 in connection with RAM 1008 generally operate to execute the instructions stored in non-volatile memory 1004. As one of ordinarily skill in the art will appreciate, the N processing components 1010 may include a video processor, modem processor, DSP, graphics processing unit (GPU), and other processing components.

The transceiver component 1012 includes N transceiver chains, which may be used for communicating with external devices via wireless networks. Each of the N transceiver chains may represent a transceiver associated with a particular communication scheme. For example, each transceiver may correspond to protocols that are specific to local area networks, cellular networks (e.g., a CDMA network, a GPRS network, a UMTS networks), and other types of communication networks.

It should be recognized that FIG. 11 is merely exemplary and in one or more exemplary embodiments, the functions described herein may be implemented in hardware, software, firmware, or any combination thereof. If implemented in software, the functions may be stored on or transmitted over as one or more instructions or code encoded on a non-transitory computer-readable medium 1004. Non-transitory computer-readable medium 1004 includes both computer storage medium and communication medium including any medium that facilitates transfer of a computer program from one place to another. A storage medium may be any available medium that can be accessed by a computer.

In some examples, the mobile computer device 1000 is embodied by a wearable such as a smartwatch (e.g. Apple Watch) or fitness tracker (e.g. FitBit). Alternatively, the mobile computer device 1000 is in connection with a smartwatch or fitness tracker.

Embodiments of the present method can have specific industrial applications, for example:
 as an automated tool for measuring retina vessel calibers in large population-based studies.
 as an automated assistant for clinicians and graders to get a second opinion. as a standalone on-demand risk assessment of cardio-vascular diseases over the Internet.

It will be appreciated that many further modifications and permutations of various aspects of the described embodiments are possible. Accordingly, the described aspects are intended to embrace all such alterations, modifications, and variations that fall within the spirit and scope of the appended claims.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The invention claimed is:

1. A method for training a neural network for automated retina vessel measurement, comprising:
receiving a plurality of fundus images;
pre-processing the fundus images to normalise images features of the fundus images; and
training a multi-layer neural network on the pre-processed fundus images, the neural network comprising convolutional unit, multiple dense blocks alternating with transition layers or transition units for down-sampling image features determined by the neural network, and a fully-connected unit, wherein each dense block comprises a series of cAdd units packed with multiple convolutions, and each transition layer or transition unit comprises a convolution with pooling.

2. The method of claim 1, further comprising grouping the input channels of each cAdd unit into non-overlapping groups and adding the outputs of the cAdd unit to one of the non-overlapping groups, thus forming the inputs to a next cAdd unit in the series, and for successive ones of said cAdd units, the output of a previous cAdd unit in the series is added to a different one of said non-overlapping groups.

3. The method of claim 1, further comprising:
automatically detecting a centre of an optic disc in each fundus image; and
cropping the respective image to a region of predetermined dimensions centred on the optic disc centre.

4. The method of claim 1, wherein pre-processing the fundus images comprises applying global contrast normalisation to each fundus image.

5. The method of claim 3, wherein pre-processing the fundus images further comprises median filtering using a kernel of predetermined size.

6. The method of 1, wherein there are five dense blocks in the multiple dense blocks.

7. The method of claim 1, wherein each dense block comprises a series of cAdd units packed with two types of convolutions.

8. The method of claim 7, wherein the two types of convolutions comprise a 1×1 convolution and a 3×3 convolution.

9. The method of claim 1, wherein the convolution of each transition layer or transition unit is a 1×1 convolution.

10. A method of quantifying vessel calibre of a retina fundus image, comprising:
receiving a retina fundus image; and
applying a neural network trained according to the method of claim 1 to the retina fundus image.

11. A computer system for training a neural network to generate retina vessel measurements, comprising:
a memory; and
at least one processor, the memory storing a multi-layer neural network and instructions that, when executed by the at least one processor cause the at least one processor to:
receive a plurality of fundus images;
pre-process the fundus images to normalise images features of the fundus images; and
train the neural network on the pre-processed fundus images, the neural network comprising a convolutional unit, multiple dense blocks alternating with transition units or transition layers for down-sampling image features determined by the neural network, and a fully-connected unit, wherein each dense block comprises a series of cAdd units packed with multiple convolutions, and each transition unit or transition layer comprises a convolution with pooling.

12. The computer system of claim 11, wherein the instructions further cause the processor to group the input channels of each cAdd unit into non-overlapping groups and adding the outputs of the cAdd unit to one of the non-overlapping groups, thus forming the inputs to a next cAdd unit in the series, and for successive ones of said cAdd units, the output of a previous cAdd unit in the series is added to a different one of said non-overlapping groups.

13. The computer system of claim 11, wherein the instructions further cause the processor to:
automatically detect a centre of an optic disc in each fundus image; and
crop the respective image to a region of predetermined dimensions centred on the optic disc centre.

14. The computer system of claim 11, wherein the instructions cause the processor to pre-process the fundus images by applying global contrast normalisation to each fundus image.

15. The computer system of claim 11, wherein there are five dense blocks in the multiple dense blocks.

16. The computer system of claim 11, wherein each dense block comprises a series of cAdd units packed with two types of convolutions.

17. The computer system of claim 16, wherein the two types of convolutions comprise a 1×1 convolution and a 3×3 convolution.

18. The computer system of claim 11, wherein the convolution of each transition unit or transition layer is a 1×1 convolution.

19. The computer system of claim 11, wherein the neural network is trained on the pre-processed fundus images to quantify a vessel calibre of a retina fundus image.

* * * * *